United States Patent [19]

Gehatia et al.

[11] 4,043,669

[45] Aug. 23, 1977

[54] LIGHT SCATTERING TEST APPARATUS

[75] Inventors: Matatiahu Gehatia; Donald R. Wiff, both of Dayton, Ohio

[73] Assignee: The United States of America as represented by the Secretary of the Air Force, Washington, D.C.

[21] Appl. No.: 691,162

[22] Filed: May 28, 1976

[51] Int. Cl.[2] .............................................. G01N 21/00

[52] U.S. Cl. .................................... 356/104; 250/574; 356/246

[58] Field of Search ............... 356/103, 104, 207, 208, 356/246; 250/574

[56] References Cited

U.S. PATENT DOCUMENTS

| | | | |
|---|---|---|---|
| 2,858,727 | 11/1958 | Stamm et al. | 356/104 |
| 3,508,830 | 4/1970 | Hopkins et al. | 356/103 |
| 3,811,780 | 5/1974 | Liston | 356/246 X |

FOREIGN PATENT DOCUMENTS

| | | | |
|---|---|---|---|
| 2,791,372 | 7/1972 | Japan | 356/103 |
| 1,094,779 | 12/1967 | United Kingdom | 356/104 |

*Primary Examiner*—John K. Corbin
*Assistant Examiner*—Matthew W. Koren
*Attorney, Agent, or Firm*—Joseph E. Rusz; Richard J. Killoren

[57] ABSTRACT

An apparatus for measuring light scattered at various angles from a sample of molecules in solution, having a plurality of conical reflectors mounted on a turret assembly. The turret assembly is positioned in a temperature controlled tank. A laser beam is directed through the tank with the polymer sample being positioned within one of said reflectors in the path of the laser beam. Light scattered at a particular angle is collected and directed to a detector. The unscattered light is also directed toward the detector along a second path. A light chopper is provided to alternately supply scattered light and the unscattered light beam to the detector. The laser beam path through the sample can be reversed to provide a measure of back scattered light. Each of the conical mirrors may be selectively locked in position for positioning the polymer sample in the light path.

4 Claims, 7 Drawing Figures

LASER 26
24
14
13
15
23
4
4
22
21
25
21'
12
16
42
31
13
43

14
13
13
12

61
68
50
78
74
66
76
72
70
80

LASER
10
23
24
26
27
28
33
34
36
38
40
41
44
45
45
46
47
48
49
50
52
54
56
57
58
59
61
62
63
64
65
81
82
84
86
88
90
90

LIGHT SCATTERING TEST APPARATUS

RIGHTS OF THE GOVERNMENT

The invention described herein may be manufactured and used by and for the Government of the United States for all governmental purposes without the payment of any royalty.

BACKGROUND OF THE INVENTION

This invention relates to a system for providing data for determining light scattered by molecules in solution.

A conventional light scattering system used for this purpose has a light source, an optical system for producing a monochromatic collimated light beam, a cell which contains the molecules in solution, and a device to measure the light intensity of the light scattered at some angle $\theta$.

The application of a laser light source has greatly improved the technique of light scattering measurement by providing a highly collimated monochromatic beam of light. However, the excessive intensity may cause emanation of heat along the path of the beam which in turn may disturb the delicate thermal balance required by the theory. New methods have been developed which are not based on increased intensity of the beam, but rather upon more efficient methods of collecting the scattered light. The U.S. Pat. No. to Hopkins et al, 3,508,830, shows one such system.

BRIEF SUMMARY OF THE INVENTION

According to this invention, a light scattering system is provided for more readily measuring scattered light at various angles $\theta$. The sample is positioned in one of a plurality of conical mirrors, which are supported on a turret. The turret assembly is located in a constant temperature bath, which is important for analytical light scattering measurements.

A system is provided for comparing the light intensity in the unscattered light, passing through the sample, with the light scattered at a particular angle. A light chopper alternately supplies the scattered light signal and the unscattered beam to a single photomultiplier so that the response characteristics for both measurements will be the same. Polarizer-Analyzer attenuators are provided in the unscattered light paths to provide data from which the ratio is scattered light to unscattered light may be determined.

IN THE DRAWING

DETAILED DESCRIPTION OF THE INVENTION

Figure 1:
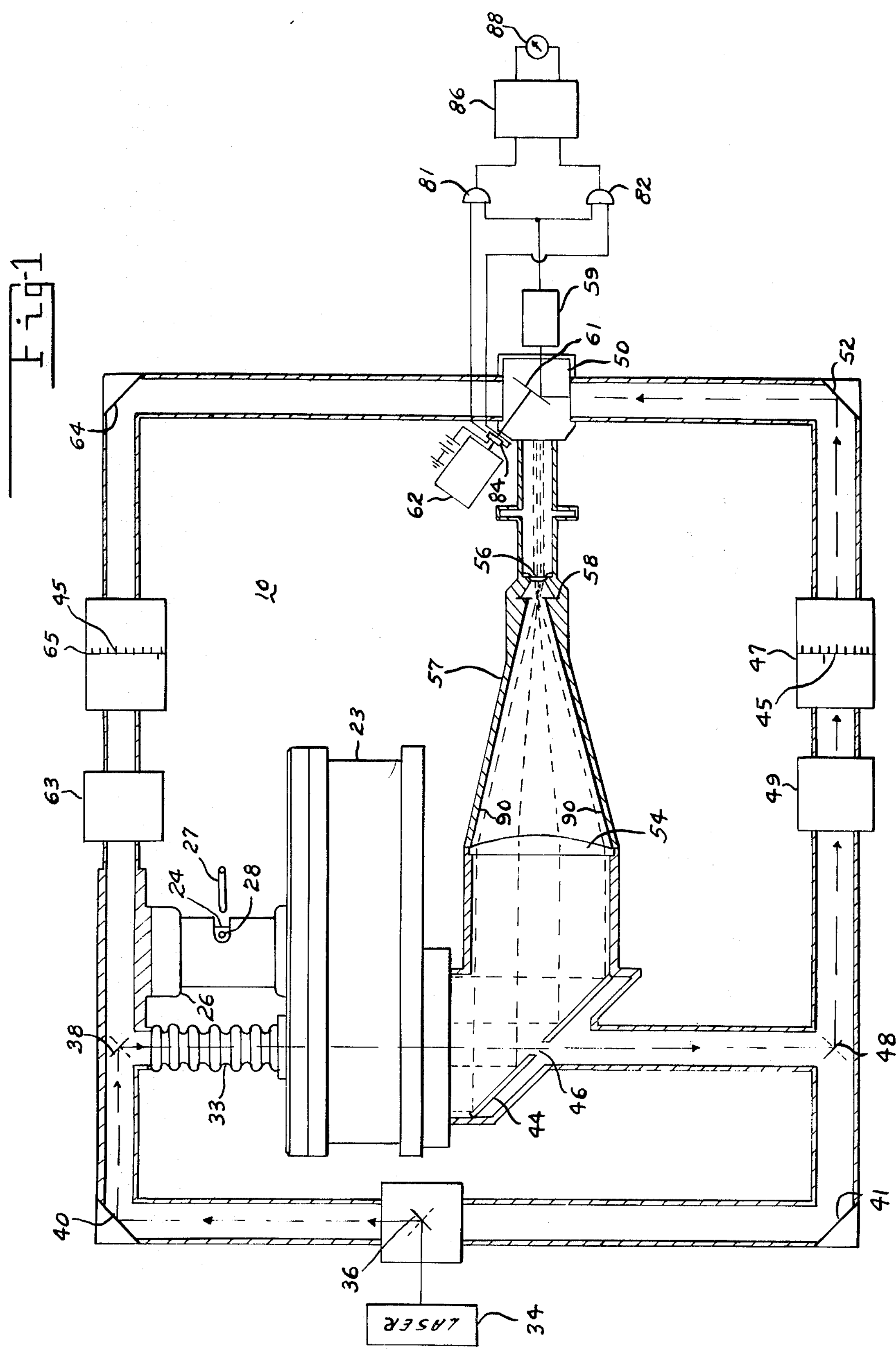
FIG. 1 is a schematic diagram of a light scattering system according to the invention.
Figure 3:
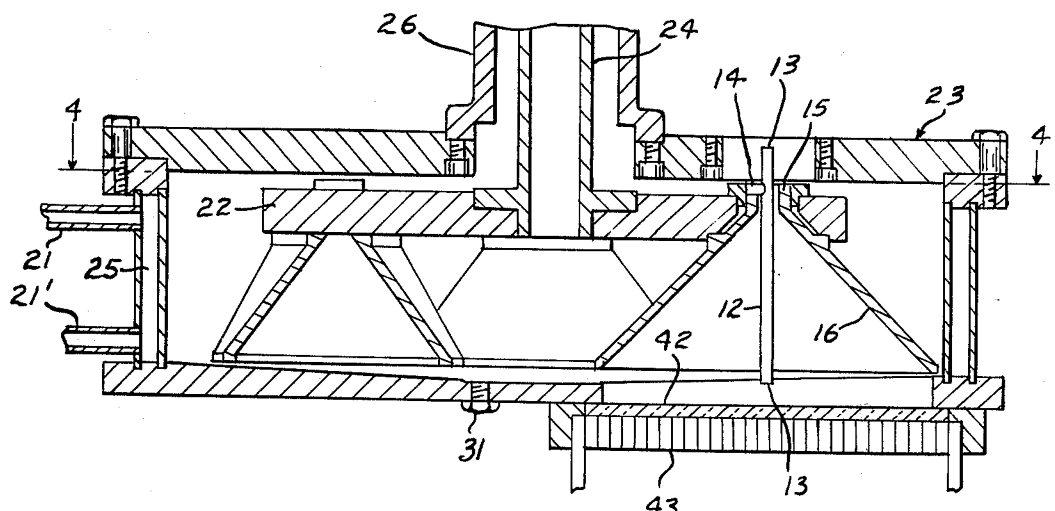
FIG. 3 is a sectional view of the device of FIG. 2, taken along the line 3—3.

Reference is now made to FIG. 1 of the drawing which shows a light scattering test apparatus 10 wherein a sample of molecules in solution, in test cell 12, is positioned in a sample tube holder 15, as shown in FIG. 3.

Figure 5:
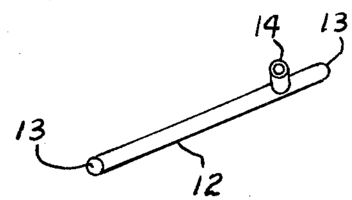
FIG. 5 is an enlarged isometric view of the test cell used in the device of FIG. 1.

The test cell 12, shown in greater detail in FIG. 5, is closed at ends 13 with the test specimen being supplied through filler tube 14 which may be closed with wax. The specimen filler tube 14 aids in holding the test cell 12 in sample tube holder 15.

Figure 2:
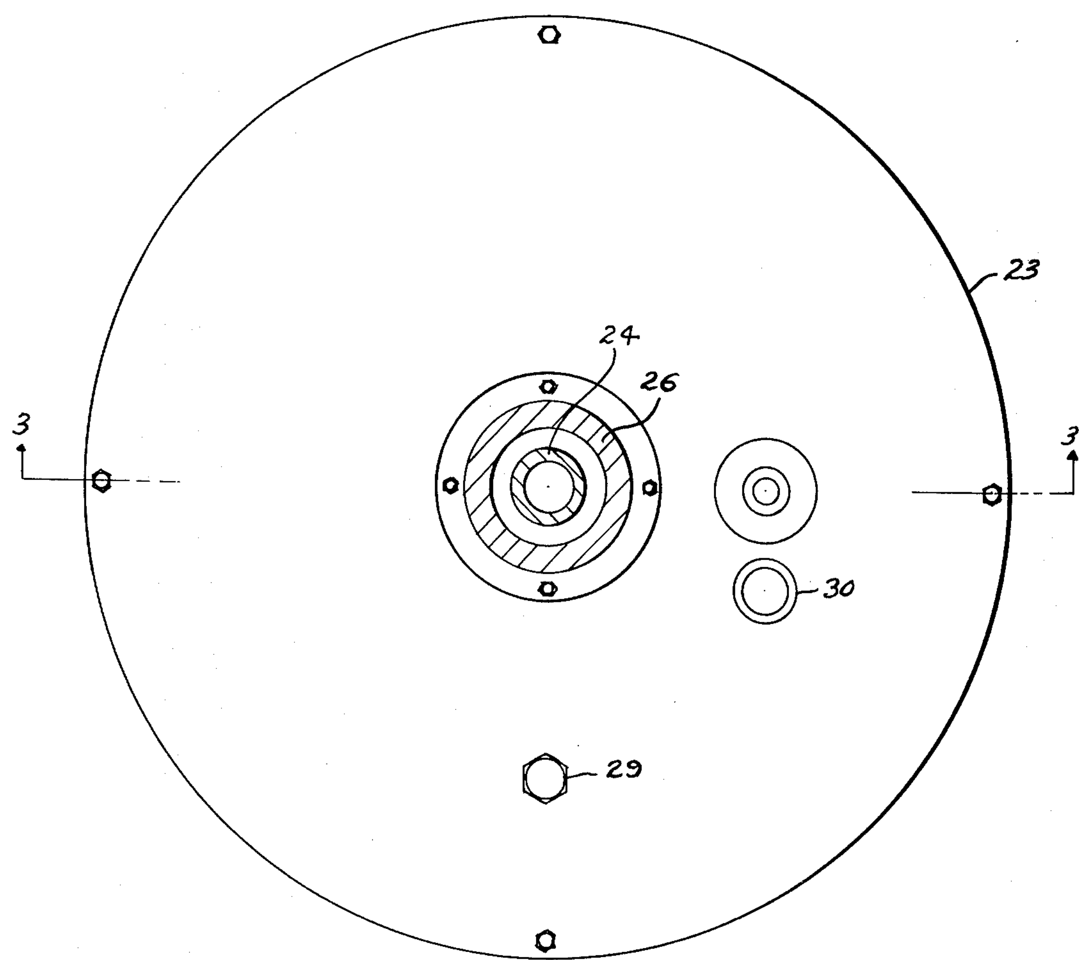
FIG. 2 is a top view of the temperature control tank for the device of FIG. 1.
Figure 4:
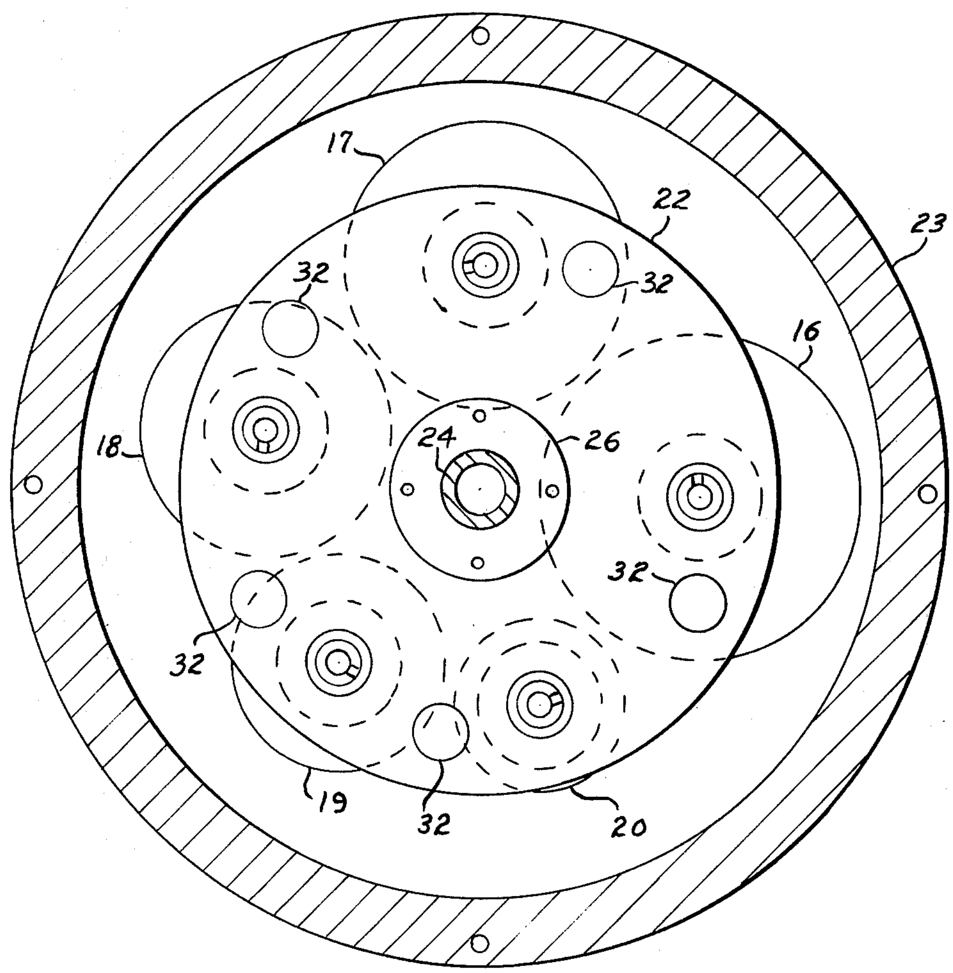
FIG. 4 is a sectional view of the device of FIG. 3, taken along the line 4—4.

The sample tube holder 15 forms part of a conical mirror 16 which surrounds the test cell 12. The mirror 16 is one of five conical mirrors, 16, 17, 18, 19 and 20, shown in FIG. 4, mounted on a turret assembly 22, within a constant temperature tank, 23. The constant temperature tank 23 holds a liquid which is preferably the same liquid used in the test cell 12 for dissolving the molecules. However, other liquids having an index of refraction almost identical to the liquid in the test cell may be used. The liquid may be supplied to tank 23 at 29, shown in FIG. 2 and removed at drain 31, shown in FIG. 3. The liquid in tank 23 is cooled be a coolant supplied through tubes 21 and 21' to the heat exchanger 25 in the wall of tank 23. The turret assembly 22 is mounted on a shaft 24 which turns in a bearing, not shown, in housing 26. The housing 26 is secured to tank 23. The turret assembly 22 is turned by placing a bar 27 in holes 28, one of which is shown in FIG. 1. The turret assembly is locked in position by means of a bar 30 which passes through a hole in the top of tank 23 and engages one of the holes 32, shown in FIG. 4, in the turret assembly 22. The holes 32 are positioned a predetermined distance from the centers of mirrors 16, 17, 18, 19 and 20 and serve to lock one of the conical mirrors in position for holding the test sample. A bellows 33 is retracted so that the test cell may be inserted in the tube holder 15.

Light from laser 34 is directed by movable mirrors 36 and 38 and a fixed mirror 40 through the test cell 12. The laser used was a Spectra Physics Neon-Helium laser 123.

The conical mirrors, 16, 17, 18, 19 and 20 have angles of 45°, 37.5°, 30°, 22.5°and 15°, respectively, to direct light at scattering angles 90°, 75°, 60°, 45°and 30°, respectively, through a transparent window 42, which is sealed in the bottom of cooling tank 23. The light passing through the window 42 is directed through a collimator 43 toward a mirror 44, which is positioned at an angle of 45° with respect to the longitudinal axis of test cell 12. The collimator used is made of honeycomb material coated internally to prevent reflections. The mirror 44 has a central aperture 46 for passing light not scattered by the sample. The light passing through aperture 46 is directed by mirror 48 through variable neutral density filter 49 and then through a light attentuating polarizer-analyzer 47 by means of a movable mirror 48 and is then directed toward a light chopper 50 by a fixed mirror 52.

Figure 6:
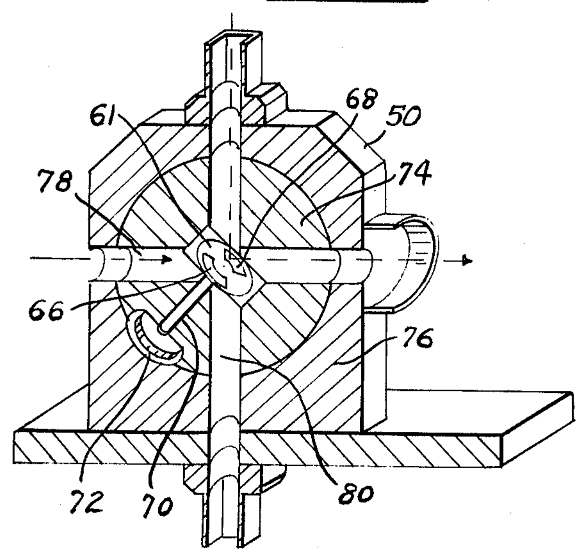
FIG. 6 is partially schematic isometric cross section of the light chopper of FIG. 1.

The light mirror 44 directs the scattered light through condenser lens 54 and collimating lens 56 without housing 57 and through a mask 58 toward light chopper 50. The light chopper has a disc 61 driven by motor 62. The light chopper may be as shown in FIG. 6 wherein a disc 61 has an area 66 which passes light to the photomultiplier 59 and a mirror 68 to reflect light to the photomultiplier 59. The disc is driven by a shaft 70 and pulley 72 which is driven by motor 62, not shown in FIG. 6. The light chopper and motor are mounted on a support member 74 which may be rotated in frame 76. Rotation of support member 74 within frame 76 permits the alignment of either passage 78 or 80 to pass scattered light to the photomultiplier. In the position shown in FIG. 1, light from mirror 52 is reflected toward the photomultiplier 59 by mirror 68. In the position shown in FIG. 7, light from mirror 64 is reflected by mirror 68 toward the photomultiplier 59.

The output of the photomultiplier 59 is applied to a pair of gate circuits 81 and 82 which are gated by signals from commutator 84.

The gate circuits 81 and 82 connect the output of the photomultiplier 59 to a differential amplifier 86 with the output of the differential amplifier being supplied to a null meter 88.

Light absorbing material 90 is provided within housing 57. Light scattered at angles other than the desired angle will be intercepted by the collimator 43 and will not reach the mirror 44.

Figure 7:
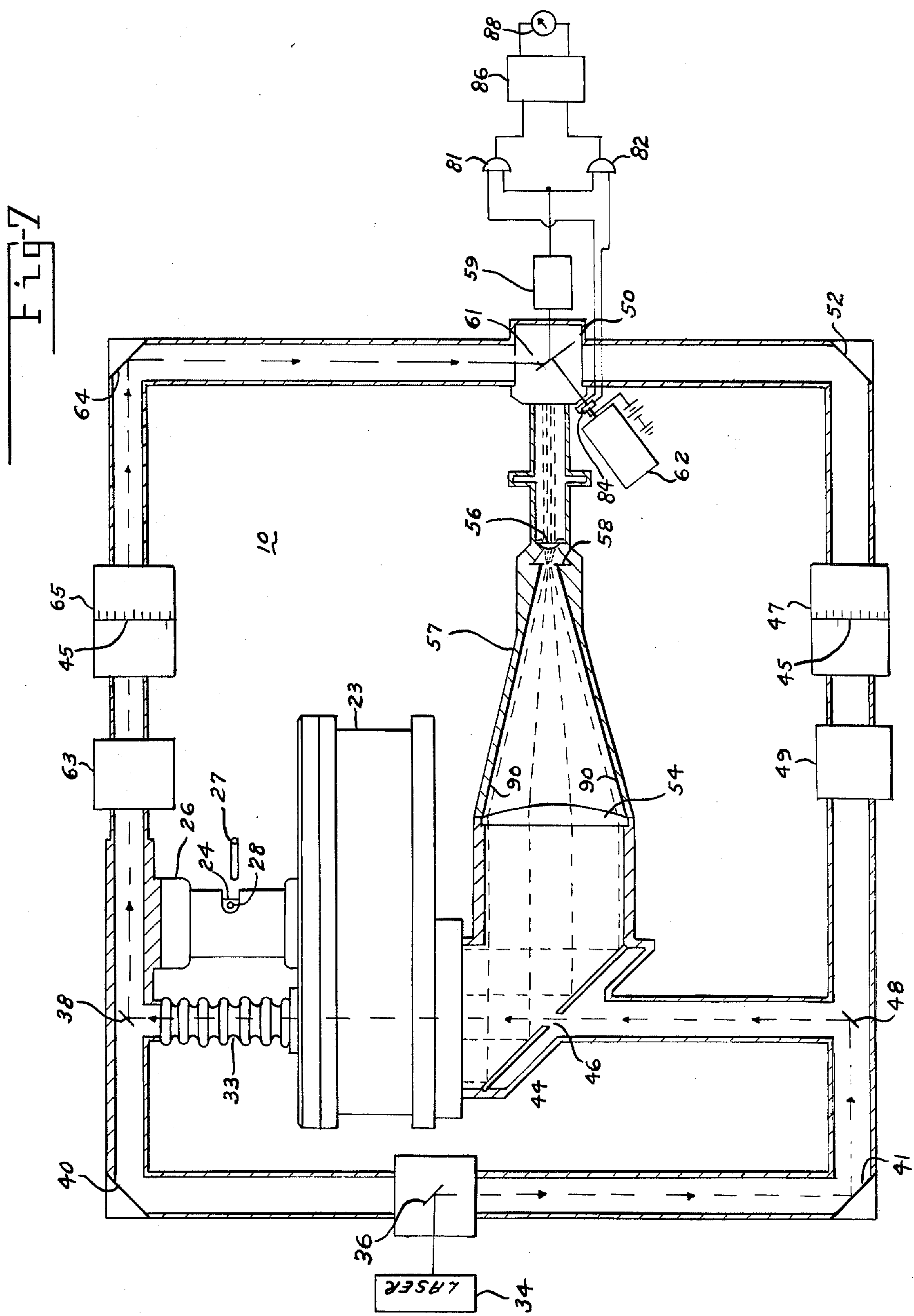
FIG. 7 shows the device of FIG. 1 with the light path reversed.

The device of FIG. 1 may be adjusted as shown in FIG. 7 to sense back scattered light. Mirrors 36, 38, 48 and light chopper 50 may be rotated 90°, as shown in FIG. 7, to cause the light to pass through the test cell 12 in the opposite direction. Light reflected off of mirror 38 then passes through a variable neutral density filter 63 and a light attenuating polarizer-analyzer 65 to mirror 64 and then to light chopper 50. The conical mirrors 17, 18, 19 and 20 then may be used to provide back scattered light at angles of 105°, 120°, 135°and 150°.

In the operation of the device of the invention, the apparatus is first calibrated. With no sample in sample holder 15, with the light chopper motor turned off, with the light chopper positioned to pass the light from mirror 52 to the photomultiplier 59 and with the polarizer-analyzer 47 set for maximum transmission, a current reading is taken from the output of the photomultiplier with a meter, not shown. The light chopper and mirrors 36, 38 and 48 are then positioned to pass light from mirror 64 to the photomultiplier 59 with polarizer-analyzer 65 set for maximum transmission. One of the variable density filters 49 or 63 is adjusted to provide the same photomultiplier output for the two light paths through the apparatus.

The quantity generally measured in most light scattering methods is the Rayleigh ratio which is proportional to $(Is/Io)_\theta$ where $I_s$ is the light scattered as some angle $\theta$ and Io is the incident light. In the apparatus of the invention, the actual light used for Io is the light transmitted through the sample which is very close in value to the light incident on the sample. No great error is introduced by using the transmitted light since the scattered light intensity is less than 1/1000,000 of the intensity of either the incident or transmitted light.

With mirror 16 positioned to receive a sample cell, the test cell 12 is positioned in the sample holder 15. With mirrors 36, 38 and 48 positioned to pass light through the test cell in the forward direction, shown in FIG. 1, the laser 34 and motor 51 are started. The polarizer-analyzer 47 is then adjusted until a null is shown on meter 88. When a null is shown on meter 88, the output of the polarizer-analyzer 47 is equal to the scattered light intensity from mirror 44 scattered at 90° from the sample. Collimator 43 removes light scattered at other angles.

It is known that the light intensity $I_l$ that passes through a polarizer-analyzer is related to the incident light $I_o$ as follows:

$$I_1 = \frac{I_o}{2} \cos^2\alpha$$

where $\alpha$ is the angle between the planes of transmission of transmission of polarizer and the analyzer. Therefore, $\cos^2\alpha = (2I_1/I_o)$ so that by squaring the cosine of the angular reading, from a scale shown schematically at 45, polarizer-analyzer attenuators 47 or 65, a value proportional to Is/Io is obtained where Is is the scattered light intensity at 90 degrees and Io is the intensity of the unscattered light.

The ratio $(ir_s^2/I_o)_\theta$ is known as the Rayleigh ratio $R_{74}$. To use the device of the invention to determine the Rayleigh ratio for a substance in test cell 12, a calibration constant must be determined for each mirror 16–20 used.

If a substance is used in test cell 12, for example a standard salt solution for which the Rayleigh ratio has been determined in a conventional manner such as by the measurement of turbidity with a Cary recording spectrophotometer, a value (Is/Io) can be determined for each of the angles $\theta$ as determined by the mirrors 16–20. An explanation of the relation between turbidity and Rayleigh's ratio is given on page 13 of "Light Scattering in Physical Chemistry" by K. A. Stacey. The constant for the apparatus can then be determined from the following:

$$R_\Theta = \left(\frac{Is}{Io_\Theta}\right) K_\Theta \quad \text{or} \tag{1}$$

$$K_\Theta = \left(\frac{R_\Theta}{\frac{Is}{Io_\Theta}}\right) \tag{2}$$

The constant for the apparatus with each mirror can then be used to determine the Rayleigh ratio for other substances.

There is thus provided an apparatus for providing an indication of the ratio of the scattered light intensity to the unscattered light intensity for various solutions, at various angles and which overcomes some of the disadvantages of using a high intensity laser beam in making light scattering measurements.

We claim:

1. An apparatus for obtaining data for determining the ratio of scattered light intensity to unscattered light intensity from a sample of molecules in solution; comprising an elongated test cell containing the sample solution; means for maintaining said sample at a substantially constant temperature; means for passing a beam of monochromatic light in a longitudinal direction through said test cell; a photomultiplier; means for passing light scattered by said sample solution along a first light path toward said photomultiplier; means for passing unscattered light passing through said sample solution along a second path toward said photomultiplier; means for removing substantially all the scattered light from the sample solution, in said first path, except light scattered at a predetermined angle; means in said first and said second light paths for alternately passing light from the first and second light paths to said photomultiplier; a null indicating device connected to the output of said photomultiplier; means for attenuating the light in the unscattered light path to provide a null reading on said null meter; means for providing an indication of the attenuation needed to provide a null in the output of said photomultiplier, to thereby obtain data for determining the ratio of scattered light intensity to unscattered light intensity; said means for maintaining said sample at a substantially constant temperature including a constant temperature tank; a liquid coolant within said tank; a heat exchanger in the wall of said tank; means for supplying coolant to the heat exchanger; a turret assembly within said tank; a plurality of conical mirrors, each having a different cone angle, mounted on said turret assembly; means for rotating said turret assembly to selectively position one of said conical mirrors around the beam path of light passing through the test cell; each of said mirrors including means for holding the test cell.

2. The device as recited in claim 1 wherein said means for removing substantially all of the scattered light from the sample solution, in the first path, except light scattered at a predetermined angle, includes a collimater positioned adjacent the bottom of said tank; a flat mirror for passing scattered light from the conical mirror toward said photomultiplier; said flat mirror having a hole therein for passing unscattered light passing through the test cell along the second path; a mask, having an aperture, between the flat mirror and the photomultiplier; a condensing lens between said flat mirror and said mask for focusing light from said flat mirror on said aperture; a collimating lens between said mask and said photomultiplier.

3. The device as recited in claim 2 wherein said means for attenuating the light in the unscattered light path includes a polarizer-analyzer attenuator; said polarizer-analyzer including means for indicating the angle between the planes of transmission of the polarizer and the analyzer.

4. The device as recited in claim 3 including means for reversing the direction of the light beam path through the sample cell; said means for reversing the direction of the light beam path through said sample includes means for directing unscattered light along a third beam path toward said photomultiplier; a second polarizer-analyzer attenuator in said third beam path; said second polarizer-analyzer attenuator including means for indicating the angle between the planes of transmission of the polarizer and analyzer.

* * * * *

UNITED STATES PATENT AND TRADEMARK OFFICE

CERTIFICATE OF CORRECTION

PATENT NO. : 4,043,669

DATED : August 23, 1977

INVENTOR(S) : Matatiahu Gehatia and Donald R. Wiff

It is certified that error appears in the above-identified patent and that said Letters Patent are hereby corrected as shown below:

Column 4, line 16, change "$R_{74}$" to --- $R_\theta$ ---.

Signed and Sealed this

*Twenty-first* Day of *March 1978*

[SEAL]

*Attest:*

RUTH C. MASON
*Attesting Officer*

LUTRELLE F. PARKER
*Acting Commissioner of Patents and Trademarks*